United States Patent [19]
Rohe et al.

[11] Patent Number: 4,940,452
[45] Date of Patent: Jul. 10, 1990

[54] MAGNETIC COUPLING

[75] Inventors: Karl-Heinz Rohe, Haan; Kurt Sauerwein, Kattendahl 7, 4006 Erkrath; Karl Weinlich, Wuppertal; Rainer Link, Kerpen-Horrem; Norbert Kinzer, Wuppertal, all of Fed. Rep. of Germany

[73] Assignee: Kurt Sauerwein, Fed. Rep. of Germany

[21] Appl. No.: 232,753

[22] Filed: Aug. 16, 1988

[30] Foreign Application Priority Data
Sep. 23, 1987 [DE] Fed. Rep. of Germany ....... 3731946

[51] Int. Cl.$^5$ ...................... A61N 5/10; A61M 37/00
[52] U.S. Cl. ..................................... 600/7; 250/497.1; 403/12; 403/DIG. 1
[58] Field of Search ................ 600/1, 3, 7; 250/496.1, 250/497.1; 403/DIG. 1, 12

[56] References Cited
U.S. PATENT DOCUMENTS
2,623,256 12/1952 Feibelman ................... 403/DIG. 1

*Primary Examiner*—Kyle L. Howell
*Assistant Examiner*—John C. Hanley
*Attorney, Agent, or Firm*—Toren, McGeady & Associates

[57] ABSTRACT

A magnetic coupling for translatorily movable bodies that is made in one position, is arranged so that it can be broken, without external control, in another position. For this purpose the first body has a coupling element of permanently magnetic or magnetizable material, the second body has at least one complementary coupling element of permanently magnetic or magnetizable material, and a third body has a coupling element of permanently magnetic or magnetizable material cooperating with the second body. Arranged between the complementary coupling element of the second body and the coupling element of the third body that is a spacer which can be moved as desired between the working positions.

12 Claims, 1 Drawing Sheet

MAGNETIC COUPLING

TECHNICAL FIELD OF THE INVENTION

The invention relates to a magnetic coupling between translatorily movable bodies.

BACKGROUND OF THE INVENTION AND PRIOR ART

A coupling of this kind is described in EP-OS No. 0 158 630 in connection with a medical, therapeutic device for safely inserting radioactive radiation sources into radiation devices embedded in the human body. This device has at least one loading and/or storage station for the radiation source and at least one conveying device for the radiation source; it comprises one or more identical modules which each comprise a loading and/or storage station for the respective radiation sources with a protective radiation screening, a conveying device and a radiation device which is to be introduced into the human body and can be uncoupled from the conveying device. For this purpose a coupling is arranged between the radiation source and the conveying device which can release or break the connection in the radiation position. This coupling consists of permanent magnets or magnetizable bodies which are connected to the conveying device and permanent magnets or magnetizable bodies cooperating therewith on the radiation source. This known magnetic coupling is intended to be released in the region of the radiation device by operating spring-loaded slides.

Since the radiation device is implanted it should be as small as possible, have no external operating connections of any kind and not present any radiation risks for the hospital personnel when being operated.

OBJECT OF THE INVENTION

The object of the invention is therefore to provide a magnetic coupling between translatorily movable bodies which in the end phase of the translatory movement can be coupled or uncoupled from the outside without assistance.

BRIEF DESCRIPTION OF THE INVENTION

This object is achieved in a magnetic coupling of the kind mentioned above if the first body has a coupling element according to the invention of permanently magnetic or magnetizable material, the second body has at least one complementary coupling element of permanently magnetic or magnetizable material, and a further body has a coupling element, cooperating with the second body, of permanently magnetic or magnetizable material and a spacer that can be adjusted as desired between two different working positions is arranged between the complementary coupling element of the second body and the coupling element of the third body.

By adjusting the spacer the holding force between the complementary coupling element of the second body and the coupling element of the third body can be varied from a maximum at the smallest distance to a predetermined minimum which still ensures a sufficient coupling effect between the second and the third body. If the spacer is now set so that the second body is coupled to the third body with relatively small holding force, it is held by the coupling element of the first body as soon as the second body comes into the neighbourhood of the first body. The holding force of the coupling element of the third body is then no longer sufficient to move the second body with the aid of the complementary coupling element out of the neighbourhood of the first body so that the third body is released from the second body.

If the second body is now to be moved back out of the neighbourhood of the first body, the spacer is adjusted so that the coupling element of the third body is right up against the complementary coupling element of the second body. The attractive force between these two coupling elements now exceeds the attractive force between the complementary coupling element and the coupling element of the first body, so that a movement of the third body moves the second body out of the neighbourhood of the first body. The coupling elements can all consist of permanently magnetic material. It is also possible to manufacture only two of the three coupling elements of permanently magnetic material while the third coupling element consists of magnetizable material. Finally, it is also possible to make only the complementary coupling element of magnetic material and to make the two other coupling elements of magnetizable material.

In all three cases, the strength of the magnets and the distance given by the spacer in both working positions is predetermined so that a reliable coupling or release of the coupling is guaranteed in the predetermined positions.

The spacer preferably consists of a displaceable sleeve surrounding the third body whose two working positions are determined by a locking device acting between the sleeve and the third body which can be released by a predetermined force.

The first body preferably consists of a sleeve which accommodates the second body and of which one end forms a stop for the spacer. In this manner, according to the position of the spacer, it is ensured that the coupling element of the first body and the complementary coupling element of the second body are the right distance apart for coupling or uncoupling.

The respective ends of the bodies facing one another serve as coupling elements.

To enable the spacer to be adjusted in the end position of the second and the third body away from the first body there is arranged in the path of movement of the third body a housing with a fixed stop and a stop for the spacer that can be moved as desired. If the body with the spacer is brought up against the fixed stop, the spacer is moved into one working position, while it is moved into the other working position if the movable stop is put in the path of movement of the body with the spacer and the body with the spacer is moved up against this stop. In this manner, the magnetic coupling according to the invention can always be programmed so that it brings the second body up to the first body and leaves it there, or releases it from the first body and brings it back to the starting position.

The magnetic coupling according to the invention can be used to particular advantage if the first body is part of a hollow radiation device, for example one that is implanted in the human body, the second body is part of a radiation source which can be brought into the radiation device, and the third body and the spacer are fixed to the end of a flexible but axially stiff cable guided in a sheath.

BRIEF DESCRIPTION OF THE DRAWINGS

The invention will now be described in more detail with reference to an exemplary embodiment shown in the drawings, in which.

DETAILED DESCRIPTION OF A PREFERRED EMBODIMENT OF THE INVENTION

Figure 1:
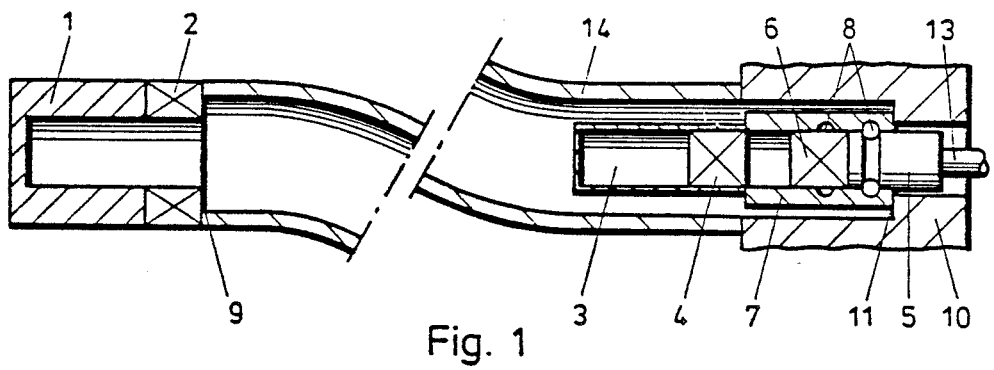
FIG. 1 shows, in the starting position, the magnetic coupling according to the invention as part of a device for safely inserting radioactive radiation sources into an interstitially inserted radiation device.

A device for inserting radioactive radiation sources into an interstitially inserted radiation device is described in detail in DE-OS No. 0 158 630, in particular the interstitial insertion of the radiation device into the human body and the insertion of the radioactive radiation sources into the radiating device.

Hence only the details concerning the magnetic coupling according to the invention are shown in the drawings.

The radiation device embedded in the human body comprises a body 1 formed as a sleeve having a coupling element 2 which is formed as an annular permanent magnet arranged at its open end.

A body 3 serves as a radiation source which is to be put in the cavity in the sleeve 1 so as to exert its radiation effect inside the human body. This body 3 has on its one end a complementary coupling element 4, which also consists of a permanent magnet. This complementary coupling element 4 cooperates with a body 5 whose end facing the complementary coupling element 4 has a further coupling element 6 in the form of a permanent magnet. Around the body 5 and the coupling element 6 there is a spacer 7 in the form of a displaceable sleeve which can be displaced between two working positions. For this purpose, between the body 5 and the coupling element 6 and the sleeve 7 there is a locking device 8, e.g. in the form of spring-loaded balls arranged in a bore of the body 5, and annular grooves spaced from one another in the sleeve 7.

Figure 2:
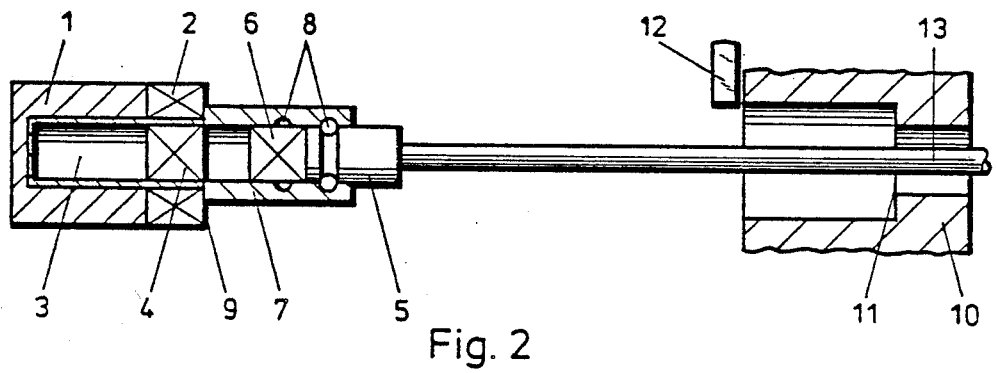
FIG. 2 shows the device according to FIG. 1 in its end position.

An end face 9 of the coupling element 2 serves as a stop for the sleeve 7 when the bodies 3 and 5, coupled with one another, are moved to the position shown in FIG. 2 by means of a flexible but axially stiff cable 13 guided in a flexible sheath 14.

Figure 3:
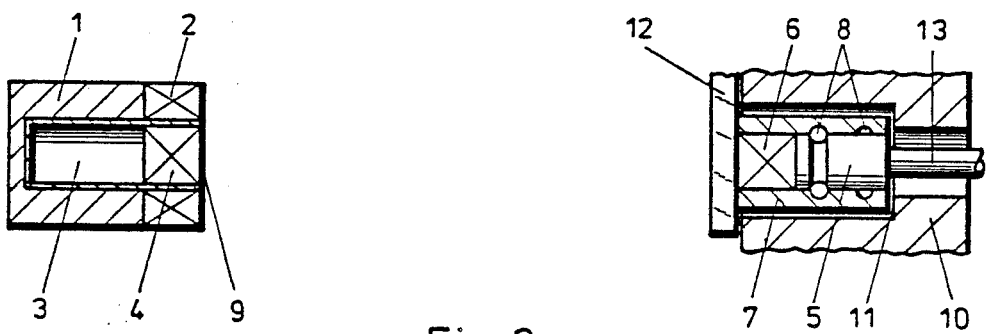
FIG. 3 shows the device according to FIG. 1 and 2 with its conveying device drawn back.
Figure 4:
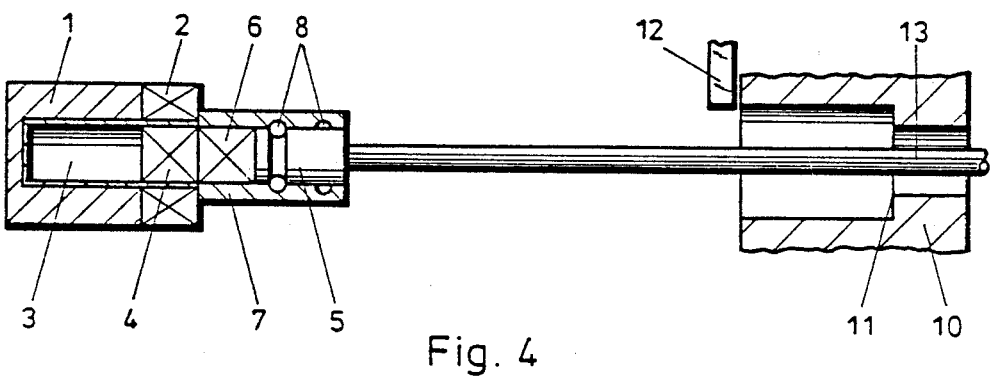
FIG. 4 shows the device according to FIGS. 1 to 3 with the conveying device advanced in order to retrieve the radiation source.

In the positions shown in FIGS. 1 and 3, the body 5 with the coupling element 6 and the sleeve 7 are in a housing 10 which is provided with a fixed stop 11 and a movable stop 12 for the spacer 7. In the position shown in FIG. 1 the body 5 is pulled so far into the housing 10 by means of the cable 13 that the sleeve 7 is displaced at the fixed stop 11 into the extreme left-hand working position shown in FIG. 1. This results in a space or air gap between the coupling element 4 and the coupling element 6 on the body 5 which is large enough to couple the body 3 with the body 5 so that it can be moved into the position shown in FIG. 2. In this position the coupling elements 2 and 4 are so close together that their mutual attractive force is greater than that between the complementary coupling element 4 and the coupling element 6. If the body 5 is then pulled back by means of the cable 13, the body 3 and the body 5 separate, the body 3 remaining in the radiation device 1 while the body 5 is pulled back again into the housing 10. If, as shown in FIG. 3, the movable stop 12 is now pushed in front of the body 5 with the spacer 7, the body 5 can be moved by means of the cable 13 into the second working position shown in FIG. 3 in which the end faces of the coupling element 6 and the sleeve 7 lie in one plane.

To withdraw the radiation source 3 from the radiation device 1 again, the body 5 is moved until there is contact between the complementary coupling element 4 and the coupling element 6. Since the complementary coupling element 4 and the coupling 6 now lie directly next to one another, their mutual attractive force is greater than that between the complementary coupling element 4 and the coupling element 2 so that the radiation source 3 can be retrieved from the radiation device 1 by moving the cable 13 back.

In this manner the radiation device 1 can be given a completely passive form with a small volume and without any control connected to it, while switching of the magnetic coupling according to the invention can be performed at a substantial distance from the radiation device 1, i.e. from outside the human body.

Not all of the coupling elements 2, 4, 6 need to consist of permanent magnets; only the complementary coupling element 4 or two of the coupling elements 2, 4, 6 need consist of permanent magnets, while the remaining coupling elements are made of a magnetizable material. Furthermore, it is not necessary for the coupling elements 4, 6 to be in contact in the one working position. It is in fact sufficient if in the one working position the holding force between the coupling element 4 and the coupling element 6 is weaker than the holding force between the coupling element 2 and the complementary coupling element 4, and in the other working position it is greater.

What is claimed is:

1. A magnetic coupling between translatorily movable bodies, comprising:
    a first body (1) having a coupling element (2) of permanently magnetic or magnetizable material;
    a second body (3) having at least one complementary coupling element (4) of permanently magnetic or magnetizable material complementary to the coupling element of the first body, the second body being insertable into the first body and being magnetically maintainable in the first body by the coupling element of the first body and the coupling element of the second body;
    a third body (5) having a coupling element (6) of permanently magnetic or magnetizable material, the coupling element of the third body being arranged so as to cooperate with the complementary coupling element of the second body so as to allow withdrawal of the second body from the first body; and
    a spacer (7), arranged so as to separate the complementary coupling element of the second body and the coupling element of the third body, the spacer being selectively movable with respect to said coupling element of said third body between two different positions.

2. A magnetic coupling element according to claim 1, wherein all three coupling elements consist of permanently magnetic material.

3. A magnetic coupling according to claim 1, wherein at least two of the three coupling elements consist of permanently magnetic material.

4. A magnetic coupling according to claim 1, wherein the complementary coupling element consists of permanently magnetic material and the two other coupling elements consist of magnetizable material.

5. A magnetic coupling according to claim 1, wherein the spacer is a displaceable sleeve surrounding the third body so that the third body is movable therewith.

6. A magnetic coupling according to claim 5, and further comprising locking means arranged between the sleeve and the third body for holding the sleeve in its two positions, said locking means being releasable by a predetermined force.

7. A magnetic coupling according to claim 5, and further comprising a housing for the displaceable sleeve, said housing having a fixed stop and a movable stop for the sleeve, said movable stop being selectively movable to maintain said sleeve in said housing between said stops.

8. A magnetic coupling according to claim 1, wherein the first body is a sleeve arranged so as to accommodate the second body, said sleeve having one end which is a stop for the spacer.

9. A magnetic coupling according to claim 7, wherein the one end of the sleeve forms the first body coupling element and faces the second body.

10. A magnetic coupling according to claim 9, wherein the second body has an end which faces the third body and forms the second body coupling element.

11. A magnetic coupling according to claim 10, wherein the third body has an end which faces the second body and forms the third body coupling element.

12. A magnetic coupling according to claim 1, wherein the first body is part of a hollow radiation device to be inserted into a human body, the second body is part of a radiation source insertable into the radiating device, and further comprising a flexible but axially stiff cable guided in a sheath, the third body being secured to an end of the cable, and the spacer being connected to the third body.

* * * * *